(12) United States Patent
Huang et al.

(10) Patent No.: US 11,441,986 B1
(45) Date of Patent: Sep. 13, 2022

(54) DISTURBANCE AND STABILITY ANALYSIS METHOD FOR HYDRATE RESERVOIRS WITH DIFFERENCE BURIED DEPTHS

(71) Applicant: Qingdao Institute of Marine Geology, Qingdao (CN)

(72) Inventors: Li Huang, Qingdao (CN); Nengyou Wu, Qingdao (CN); Xiluo Hao, Qingdao (CN); Gaowei Hu, Qingdao (CN); Qiang Chen, Qingdao (CN)

(73) Assignee: Qingdao Institute of Marine Geology, Qingdao (CN)

( * ) Notice: Subject to any disclaimer, the term of this patent is extended or adjusted under 35 U.S.C. 154(b) by 0 days.

(21) Appl. No.: 17/699,232

(22) Filed: Mar. 21, 2022

(30) Foreign Application Priority Data

Apr. 27, 2021 (CN) .......................... 202110456415.X (51) Int. Cl.
*G01N 7/14* (2006.01)
*G01N 7/16* (2006.01)
*G01N 33/24* (2006.01)

(52) U.S. Cl.
CPC ............... *G01N 7/14* (2013.01); *G01N 7/16* (2013.01); *G01N 33/241* (2013.01); *G01N 33/246* (2013.01)

(58) Field of Classification Search
CPC .......... G01N 7/14; G01N 7/16; G01N 33/241; G01N 33/246
See application file for complete search history.

(56) References Cited

U.S. PATENT DOCUMENTS

| 11,053,780 | B2 * | 7/2021 | Chen | ................ | E21B 47/07 |
| 2004/0166582 | A1 * | 8/2004 | Prinzhofer | .............. | E21B 47/11 |
| | | | | | 436/27 |

(Continued)

FOREIGN PATENT DOCUMENTS

| CN | 101046146 A | 10/2007 |
| CN | 101358685 A | 2/2009 |

(Continued)

OTHER PUBLICATIONS

Moridis et al.: "Challenges, Uncertainties and Issues Facing Gas Production From Hydrate Deposits in Geologic Systems" SPE 131792 (Year: 2010).*

(Continued)

*Primary Examiner* — John Fitzgerald (57) ABSTRACT

The present invention relates to disturbance on hydrate reservoirs with different buried depths, in particularly to a disturbance and stability analysis method for hydrate reservoirs with different buried depths. Preparing a series of stable hydrate systems parallel to a hydrate phase equilibrium curve, wherein both of the porosities and the hydrate saturations of various hydrate systems are consistent, but the buried depths are different; disturbing the series of hydrate systems prepared in the first step, conducting disturbance under different conditions aiming to the hydrate systems with different buried depths; analyzing the stability of the hydrate reservoirs. By controlling the disturbance condition, the hydrate systems with different buried depths may be decomposed along the hydrate phase equilibrium curves thereof or in the hydrate unstable regions; and the decomposition productivity difference between the hydrate reservoirs with different buried depths may be intuitively and scientifically simulated and analyzed.

6 Claims, 1 Drawing Sheet

(56) References Cited

U.S. PATENT DOCUMENTS

| | | | | |
|---|---|---|---|---|
| 2016/0305205 | A1* | 10/2016 | Li | G01N 33/241 |
| 2017/0292904 | A1* | 10/2017 | Xing | G01N 15/088 |
| 2018/0045029 | A1* | 2/2018 | Goksel | E21B 43/28 |
| 2019/0234856 | A1* | 8/2019 | Ou | G01N 33/241 |
| 2020/0232305 | A1* | 7/2020 | Chen | E21B 43/36 |
| 2022/0074915 | A1* | 3/2022 | He | G01N 33/241 |

FOREIGN PATENT DOCUMENTS

| | | | | |
|---|---|---|---|---|
| CN | 104289083 A | | 1/2015 | |
| CN | 108086960 A | | 5/2018 | |
| EP | 3670635 A1 | | 6/2020 | |
| KR | 20130125186 A | * | 11/2013 | G01N 33/225 |

OTHER PUBLICATIONS

Huang et al. "Evaluation and composition of gas production potential of the typical four gas hydrate deposits in Shenhu sarea, South China sea," Energy 204 pp. 1-17 (Year: 2020).*

Title of the Item: Fault-Block Oil and Gas Field Publication Date: Mar. 25, 2017 Name of the Author: Wang Bo et al. Article Title: Applicability of velocity string for southern Sulige cooperation area gas wells pp. 132-136.

Title of the Item: Rock and Soil Mechanics Publication Date: Sep. 10, 2012 Name of the Author: Wu Er-Lin et al. Article Title: FEM-based simulation of decomposition process of gas hydrate-bearing sediments pp. 2811-2821.

Title of the Item: Natural Gas Industry Publication Date: May 25, 2017 Name of the Author: Khlebnikov V.N. et al. Article Title: Major factors infl uencing the formation of natural gas hydrates in porous media pp. 38-45.

Title of the Item: Journal of Tianjin University(Science and Technology) Publication Date: May 15, 2019 Name of the Author: Hong Juntian et al. Article Title: Influence of Gas Hydrate Dissociation on Submarine Slope Stability Under the Undrained Condition pp. 53-59.

Title of the Item: Natural Gas Geoscience Publication Date: Apr. 10, 2007 Name of the Author: Fan Yan et al. Article Title: Feasibility Analysis on Replacement of CH4 From Hydrate Sediment by CO2 pp. 317-320.

* cited by examiner

US 11,441,986 B1

DISTURBANCE AND STABILITY ANALYSIS METHOD FOR HYDRATE RESERVOIRS WITH DIFFERENCE BURIED DEPTHS

CROSS-REFERENCE TO RELATED APPLICATIONS

The application claims priority to Chinese patent application No. 202110456415.X, filed on Apr. 27, 2021, the entire contents of which are incorporated herein by reference.

TECHNICAL FIELD

The present invention relates to disturbance on hydrate reservoirs with different buried depths, in particularly to a disturbance and stability analysis method for hydrate reservoirs with different buried depths.

BACKGROUND

Hydrates are widely distributed in seabeds and land tundras. A global hydrate exploration and core drilling result shows that the production morphology of the hydrates is diversified, showing occurrence states of veins, beds, blocks and the like; and there are further relatively large differences in enrichment concentration, occurrence depth, temperature pressure and the like of the hydrates. How to select sites for development aiming to hydrate reservoir systems with diversified production features and solve the possibly involved environmental problems is the focal point and core for development of hydrates all the time.

At present, sandy hydrate reservoirs with high permeability and high saturation are considered as the most favorable hydrate development objective, and there have been field offshore production test operations for proving the feasibility of developing the sandy hydrate reservoirs. However, when various reservoir feature parameters, such as porosities and hydrate saturations of the hydrate reservoirs, are similar, there is no unified conclusion for how to select sites for development aiming to hydrate reservoirs with different buried depths at present. Although considered from the aspect of mining process, a deep hydrate reservoir should become an important target region in the early stage of hydrate reservoir production tests as facilitating operations including production cementing, as the shallow soft formation well spacing technology has been tackled in hydrate "pilot" production in China in 2019, there is no technical barrier in the shallow reservoir development process. Therefore, how to comprehensively evaluate the stability of hydrate reservoirs with different buried depths and a productivity difference between the hydrate reservoirs with different buried depths fundamentally becomes more important and urgent.

In addition, due to the fact that the hydrates are widely distributed in seabeds and are in a stable state, when formations encounter relatively great tectonic movement, the hydrates are disturbed. If the disturbed hydrate reservoirs are still under the phase equilibrium critical condition, whether hydrate systems can be destabilized and decomposed or not at this time? If the hydrate systems can be destabilized, whether the destabilization situations of the hydrate systems with different buried depths are the same or not? At present, these problems are not clearly explained either.

SUMMARY

An objective of the present invention is to overcome the above defects in the prior art and provide a disturbance and stability analysis method for hydrate reservoirs with different buried depths. By controlling the disturbance condition, hydrate systems with different buried depths may be decomposed along hydrate phase equilibrium curves thereof or in hydrate unstable regions; and by monitoring the decomposition situation in the experimental process, a decomposition productivity difference between the hydrate reservoirs with different buried depths may be intuitively and scientifically simulated.

The technical solution of the present invention is as follows.

A disturbance and stability analysis method for hydrate reservoirs with different buried depths, comprising the following steps:

S1, preparing a series of stable hydrate systems parallel to a hydrate phase equilibrium curve, wherein both of the porosities and the hydrate saturations of various hydrate systems are consistent, but the buried depths are different; a temperature value and a pressure value of each stable hydrate system are $T_i$ and $P_i$ respectively, wherein i represents each of stable hydrate systems i with different buried depths; and the corresponding temperature values and pressure values of the hydrate systems with different buried depths need to satisfy the following condition:

$$\ln(P_i) = -1.9413850446456 \times 10^5 + 3.31018213397926 \times 10^3 (T_i + T_t) - 22.5540264493806 (T_i + T_t)^2 + 0.0767559117787059 (T_i + T_t)^3 - 1.30465829788791 \times 10^{-4} (T_i + T_t)^4 + 8.86065316687571 \times 10^{-8} (T_i + T_t)^5,$$

wherein $T_t$ is a specified numerical value with the unit of ° C.;

S2, disturbing the series of hydrate systems prepared in the first step, conducting disturbance under different conditions aiming to the hydrate systems with different buried depths, and monitoring and collecting the gas production rates $V_g$ and the water production rates $M_w$ of the systems under disturbance;

S3, analyzing the stability of the hydrate reservoirs with different buried depths based on real-time variable quantities of the gas production rates $V_g$ and the water production rates $M_w$;

in the step S1, the preparation process of the stable hydrate systems comprises the following steps:

S1.1, filling a cleaned and dried reaction kettle with a known volume $V_{hf}$ with sediment with a known density, compacting the sediment, recording a weight of the filled sediment, and covering the reaction kettle with a kettle cover; after purging with methane gas for several times, continuously injecting pure methane gas; controlling the content of the methane gas entering the reaction kettle with a gas flowmeter at $V_{CH4}$, and at this time, obtaining the quantity of the methane gas substance injected into the system: $n_{CH4} = V_{CH4}/22.4$; closing an injection valve of the reaction kettle, setting a temperature of a system as the room temperature, and waiting for the system to be stabilized; and when preparing the hydrate systems with different buried depths, enabling the injection quantities of the sediment and the injection quantities of the methane gas to be the same, wherein the unit of $V_{CH4}$ is mL, and the unit of $n_{CH4}$ is mol;

S1.2, opening the injection valve again, and injecting deionized water into the reaction kettle with the injection quantity of $V_{wi}$ (the injection quantities of the deionized water for the hydrate systems with different buried depths are different, and with increase in buried depth of the hydrate systems, the injection quantity of the deionized water is increased); after closing the valve and waiting for the system to be stabilized, cooling the reaction kettle to 0.5° C.; and after hydrates are synthesized and the hydrate systems are finally stabilized, recording an average temperature $T_{hdi}$ and a pressure $P_{hdi}$ of each system at this time, wherein the unit of $T_{hdi}$ is °C., the unit of $P_{hdi}$ is MPa and the unit of $V_{wi}$ is mL;

wherein a measuring standard of the injection quantity $V_{wi}$ of the deionized water is $$\frac{V_{wi}}{18} \geq 6n_{CH_4},$$

and the system pressure condition $P_{hdi} > P_{ei}$ is guaranteed with the injection quantity after the hydrates are synthesized, wherein $P_{ei}$ is a corresponding hydrate phase equilibrium pressure at the system average temperature $T_{hdi}$, and a calculating formula of $P_{ei}$ is as follows:

$$\ln(P_{ei}) = a_0 + a_1 T + a_2 T^2 + a_3 T^3 + a_4 T^4 + a_5 T^5, \quad (1)$$

wherein $T = T_{hdi} + 273.15$, the unit of T is K; and $a_0$-$a_5$ take values under the following conditions:

$$\begin{cases} a_0 = -1.94138504465460 \times 10^5 \\ a_1 = 3.31018213397926 \times 10^3 \\ a_2 = -2.25540264493806 \times 10^1 \\ a_3 = 7.67559117787059 \times 10^{-2} \\ a_4 = -1.30465829788791 \times 10^{-4} \\ a_5 = 8.86065316687571 \times 10^{-8} \end{cases} 0° C. < T_{hdi} \leq 25° C.,$$

$$\begin{cases} a_0 = -4.3892117343462833 \times 10^1 \\ a_1 = 7.76302133739303 \times 10^{-1} \\ a_2 = -7.27291427030502 \times 10^{-3} \\ a_3 = 3.85413985900724 \times 10^{-4} \\ a_4 = -1.03669656828834 \times 10^{-7} \\ a_5 = 1.09882180475307 \times 10^{-10} \end{cases} -25° C. \leq T_{hdi} \leq 0° C.$$

S1.3, through the formula (1), reversely solving a corresponding equilibrium temperature $T_{ei}$ at a system stabilization pressure $P_{hdi}$, slowly raising the temperature of each system to $(T_{ei} - T_t)$ at a rate of 1/4-2° C./h; wherein $T_t$ is a specific numerical value, and $T_t < T_{ei}$; and at this time, a final average temperature of the hydrate systems with different buried depths is $T_i = T_{endi} = T_{ei} - T_t$, and the pressure is $P_i = P_{hdi}$.

Wherein in the step S2, when heating disturbance is conducted on the stable hydrate systems with different buried depths by simulating hydrate disturbance caused by tectonic movement in the natural environment, the temperatures of the series of stable hydrate systems prepared in the step S1 are slowly raised to $(T_i + T_t)$ at a rate of 1/2-1° C./h, and the temperature is kept for 12 h or above, wherein $T_t$ is the specified numerical value; at this time, the hydrate systems are still under the phase equilibrium condition; and in the whole heating and temperature stabilizing process, the gas production rate $V_g$ and the water production rate $M_w$ of each system under disturbance are monitored and collected in real time.

Wherein in the step S2, when depressurization disturbance is conducted on the stable hydrate systems with different buried depths by simulating hydrate disturbance caused by tectonic movement in the natural environment, a system pressure value $P_i$ of each hydrate system is lowered to $P_{wi}$; and if hydrates after being disturbed are under the phase equilibrium condition, $P_{wi}$ satisfies the following condition:

$P_{wi} = \exp(-1.9413850446456 \times 10^5 + 3.31018213397926 \times 10^3 T_i - 22.5540264493806 T_i^2 + 0.0767559117787059 T_i^3 - 1.30465829788791 \times 10^{-4} T_i^4 + 8.86065316687571 \times 10^{-8} T_i^5);$ in the depressurization disturbance process, the gas production rate $V_g$ and the water production rate $M_w$ of each system under disturbance are monitored and collected in real time.

Wherein in the step S2, when hydrate disturbance caused by human development under depressurization is simulated, decompositions of the hydrate systems with different buried depths under depressurization to the same degree are simulated; and decomposition pressures applied to the hydrate systems with different buried depths are $P_{wi}$, and $P_{wi}$ satisfies the following condition:

$P_{wi} = \exp(-1.9413850446456 \times 10^5 + 3.31018213397926 \times 10^3 T_i - 22.5540264493806 T_i^2 + 0.0767559117787059 T_i^3 - 1.30465829788791 \times 10^{-4} T_i^4 + 8.86065316687571 \times 10^{-8} T_F^5) - P_y,$ wherein $P_y$ is a specified numerical value and takes a value of 0.5 MPa, 1 MPa, 2 MPa or 3 MPa, and $P_y < P_i$;

simulated development is conducted on the hydrate systems with different buried depths by employing different pressures $P_{wi}$, and real-time variations of the gas production rate $V_g$ and the water production rate $M_w$ of each system in the development process is monitored and collected in real time, wherein the unit of the gas production rate $V_g$ is L; and the unit of the water production rate $M_w$ is g.

Wherein in the step S3, when hydrate disturbance caused by tectonic movement in the natural environment is simulated, the stability of the hydrate reservoirs with different buried depths is analyzed based on the gas production rates $V_g$ and the water production rates $M_w$ as follows:

if Vg and Mw are increased slowly, $$\Delta \frac{V_g}{V_{hf}} \leq 0.1 \text{ L/h},$$

$\Delta M_w \leq 1$ g/min, or Vg and Mw are invariable, it shows that the hydrates are stable when the hydrate systems with the corresponding buried depths are disturbed under the hydrate phase equilibrium condition; and if $V_g$ and $M_w$ are increased continuously, it shows that the hydrates are unstable when the hydrate systems with the corresponding buried depths is disturbed under the hydrate phase equilibrium condition;

comparing the hydrate systems with different buried depths, if Vg varies significantly, $$\Delta \frac{V_g}{V_{hf}} \leq 0.1 \text{ L/h},$$

$M_w$ does not vary obviously, and $\Delta M_w \leq 1$ g/min, it shows that when the hydrate systems with the corresponding buried depths are still in the phase equilibrium condition under natural disturbance, decomposition can occur, and there is a risk of gas leakage; if Mw varies obviously, $\Delta M_w > 1$ g/min, Vg, does not vary significantly, and $$\Delta \frac{V_g}{V_{hf}} \leq 0.1 \text{ L/h},$$

it shows that the hydrate systems with the corresponding buried depths are not decomposed when being still in the phase equilibrium condition under natural disturbance; but the salinity of seawater in a region can be changed due to production of water in a water saturation system, and the in-situ ecological environment is destroyed.

Wherein in the step S3, when the hydrates are disturbed by simulating human development under depressurization, the stability of the hydrate reservoirs with different buried depths is analyzed based on the gas production rates $V_g$ and the water production rates $M_w$ as follows:

if the gas production rates $V_g$ and the water production rates $M_w$ of the hydrate systems with different buried depths in the decomposition process are similar, it shows that the productivity advantages of the hydrate systems with different buried depths during decomposition under depressurization to the same degree are similar, and thus the effect of a depth or a temperature pressure of a reservoir on the productivity is limited;

if the gas production rate $V_g$ of the hydrate system with a certain buried depth is increased more quickly, it represents that the gas production potential of the hydrate system with the buried depth is relatively high correspondingly; if the gas production rate $V_g$ shows variations in different stages, it shows that the hydrate systems with different buried depths have the staged gas production ability in the process of depressurization to the same degree;

laws of water production of the hydrate systems with different buried depths are analyzed through $$R_{GNW} = \frac{V_g^* M_{in}}{M_w},$$

wherein $M_{in}$ is the quantity of the deionized water injected when the hydrate systems with the corresponding buried depths are prepared, with the unit of mL; and the larger $R_{GNW}$ is, it shows that the better the relative economy of developing the hydrate systems with the corresponding buried depths is.

The present invention has the beneficial effects that:

by controlling the disturbance condition with the method, the hydrate systems with different buried depths may be decomposed along the hydrate phase equilibrium curves thereof or in the hydrate unstable regions; and by monitoring the decomposition situation of the hydrates in the experimental process, the decomposition productivity difference between the hydrate reservoirs with different buried depths may be intuitively and scientifically simulated and analyzed.

DETAILED DESCRIPTION OF THE EMBODIMENTS

The present invention provides a disturbance and stability analysis method for hydrate reservoirs with different buried depths, comprising the following steps.

Step 1, preparing a series of stable hydrate systems parallel to a hydrate phase equilibrium curve, wherein both of the porosities and the hydrate saturations of various hydrate systems are consistent, but the buried depths are different; a temperature value and a pressure value of each stable hydrate system are $T_i$ and $P_i$ respectively, wherein i represents each of stable hydrate systems i with different buried depths; and the corresponding temperature values and pressure values of the hydrate systems with different buried depths need to satisfy the following condition:

$$\ln(P_i) = -1.9413850446456 \times 10^5 + 3.31018213397926 \times 10^3 (T_i+T_t) - 22.5540264493806(T_i+T_t)^2 + 0.0767559117787059(T_i+T_t)^3 - 1.30465829788791 \times 10^{-4}(T_i+T_t)^4 + 8.86065316687571 \times 10^{-8}(T_i+T_t)^5,$$

wherein $T_t$ is a specified numerical value with the unit of °C.;

In this step, the preparation process of the stable hydrate systems comprises the following steps.

Firstly; filling a cleaned and dried reaction kettle with a known volume $V_{hf}$ with sediment with a known density, compacting the sediment, recording a weight of the filled sediment, and covering the reaction kettle with a kettle cover; after purging with methane gas for several times, continuously injecting pure methane gas; controlling the content of the methane gas entering the reaction kettle with a gas flowmeter at $V_{CH4}$, and at this time, obtaining the quantity of the methane gas substance injected into the system: $n_{CH4}=V_{CH4}/22.4$; closing an injection valve of the reaction kettle, setting a temperature of a system as the room temperature, and waiting for the system to be stabilized; and when preparing the hydrate systems with different buried depths, enabling the injection quantities of the sediment and the injection quantities of the methane gas to be the same, wherein the unit of $V_{CH4}$ is mL, and the unit of $n_{CH4}$ is mol.

Then, opening the injection valve again, and injecting deionized water into the reaction kettle with the injection quantity of $V_{wi}$ (the injection quantities of the deionized water for the hydrate systems with different buried depths are different, and with increase in buried depth of the hydrate systems, the injection quantity of the deionized water is increased); after closing the valve and waiting for the system to be stabilized, cooling the reaction kettle to 0.5° C.; and after hydrates are synthesized and the hydrate systems are finally stabilized, recording an average temperature $T_{hdi}$ and a pressure $P_{hdi}$ of each system at this time, wherein the unit of $T_{hdi}$ is °C., the unit of $P_{hdi}$ is MPa and the unit of $V_{wi}$ is Ml.

In the above step; wherein a measuring standard of the injection quantity $V_{wi}$ of the deionized water is $$\frac{V_{wi}}{18} \geq 6 n_{CH_4},$$

and the system pressure condition $P_{hdi} > P_{ei}$ is guaranteed with the injection quantity after the hydrates are synthesized, wherein $P_{ei}$ is a corresponding hydrate phase equilibrium pressure at the system average temperature $T_{hdi}$, and a calculating formula of $P_{ei}$ is as follows:

$$\ln(P_{ei}) = a_0 + a_1 T + a_2 T^2 + a_3 T^3 + a_4 T^4 + a_5 T^5, \quad (1)$$

wherein $T = T_{hdi} + 273.15$ the unit of T is K; and $a_0$-$a_5$ take values under the following conditions:

$$\begin{cases} a_0 = -1.94138504465460 \times 10^5 \\ a_1 = 3.31018213397926 \times 10^3 \\ a_2 = -2.25540264493806 \times 10^1 \\ a_3 = 7.67559117787059 \times 10^{-2} \\ a_4 = -1.30465829788791 \times 10^{-4} \\ a_5 = 8.86065316687571 \times 10^{-8} \end{cases} 0° \text{ C.} < T_{hdi} \leq 25° \text{ C.},$$

$$\begin{cases} a_0 = -4.3892117343462833 \times 10^1 \\ a_1 = 7.76302133739303 \times 10^{-1} \\ a_2 = -7.27291427030502 \times 10^{-3} \\ a_3 = 3.85413985900724 \times 10^{-4} \\ a_4 = -1.03669656828834 \times 10^{-7} \\ a_5 = 1.09882180475307 \times 10^{-10} \end{cases} -25° \text{ C.} \leq T_{hdi} \leq 0° \text{ C.}$$

And finally, through the formula (1), reversely solving a corresponding equilibrium temperature $T_{ei}$ at a system stabilization pressure $P_{hdi}$, slowly raising the temperature of each system to $(T_{ei}-T_t)$ at a rate of 1/4-2° C./h; wherein $T_t$ is a specific numerical value, and $T_t<T_{ei}$; and at this time, a final average temperature of the hydrate systems with different buried depths is $T_i=T_{endi}=T_{ei}-T_t$, and the pressure is $P_i=P_{hdi}$.

Step 2, disturbing the series of hydrate systems prepared in the step 1, conducting disturbance under different conditions aiming to the hydrate systems with different buried depths, and collecting the gas production rates $V_g$ and the water production rates $M_w$ of the systems under disturbance.

Step 3, based on real-time variable quantities of the gas production rates $V_g$ and the water production rates $M_w$, analyzing the stability of the hydrate reservoirs with different buried depths, and discussing the productivity situation in the destabilization process.

When hydrates disturbance caused by tectonic movement in the natural environment is simulated, after the series of stable hydrate systems are prepared, heating disturbance and depressurization disturbance may be conducted on the hydrate systems.

When heating disturbance is conducted on the hydrate systems, the temperatures of the series of stable hydrate systems prepared in the step 1 are slowly raised to $(T_i+T_r)$ at a rate of 1/2-1° C./h, and the temperature is kept for 12 h or above, wherein $T_r$ is a specified numerical value; at this time, the hydrate systems are still under the phase equilibrium condition; and the gas production rate $V_g$ and the water production rate $M_w$ of each system under disturbance are monitored and collected in real time, and the stability of the hydrate reservoirs with different buried depths is analyzed.

Depressurization disturbance is conducted on the series of hydrate systems prepared in the step 1, the disturbed hydrates are still under the phase equilibrium condition, and at this time, a system pressure value $P_i$ of each hydrate system is lowered to $P_{wi}$; wherein $P_{wi}$ satisfies the following condition:

$$P_{wi}=\exp(-1.9413850446456\times10^5+ 3.31018213397926\times10^3T_i- 22.55402644938806T_i^2+ 0.07675591177870559T_i^3-1.30465829788791\times 10^{-4}T_i^4+8.86065316687571\times10^{-8}T_i^5).$$

When the hydrate systems with different buried depths are disturbed under different depressurization conditions, the gas production rates $V_g$ and the water production rates $M_w$ of the systems under disturbance are monitored and collected in real time, and the stability of the hydrate reservoirs with different buried depths is analyzed.

when hydrate disturbance caused by tectonic movement in the natural environment is simulated, the stability of the hydrate reservoirs with different buried depths is analyzed based on the gas production rates $V_g$ and the water production rates $M_w$ as follows:

if Vg and Mw are increased slowly $$\Delta\frac{V_g}{V_{hf}} \le 0.1\ \text{L/h},$$

$\Delta M_w \le 1$ g/min, or Vg and Mw are invariable, it shows that the hydrates are stable when the hydrate systems with the corresponding buried depths are disturbed under the hydrate phase equilibrium condition; and if $V_g$ and $M_w$ are increased continuously, it shows that the hydrates are unstable when the hydrate systems with the corresponding buried depths is disturbed under the hydrate phase equilibrium condition;

comparing the hydrate systems with different buried depths, if Vg varies significantly, $$\Delta\frac{V_g}{V_{hf}} \le 0.1\ \text{L/h},$$

$M_w$ does not vary obviously, and $\Delta M_w \le 1$ g/min, it shows that when the hydrate systems with the corresponding buried depths are still in the phase equilibrium condition under natural disturbance, decomposition can occur, and there is a risk of gas leakage; if $M_w$ varies obviously, $\Delta M_w > 1$ g/min, Vg, does not vary significantly, and $$\Delta\frac{V_g}{V_{hf}} < 0.1\ \text{L/h},$$

it shows that the hydrate systems with the corresponding buried depths are not decomposed when being still in the phase equilibrium condition under natural disturbance; but the salinity of seawater in a region can be changed due to production of water in a water saturation system, and the in-situ ecological environment is destroyed.

When hydrate disturbance caused by human development under depressurization is simulated, the disturbed hydrate systems are in an unstable state, and decompositions of the hydrate systems with different buried depths under depressurization to the same degree are simulated; and decomposition pressures applied to the hydrate systems with different buried depths are $P_{wi}$, and $P_{wi}$ satisfies the following condition:

$$P_{wi}=\exp(-1.9413850446456\times10^5+ 3.31018213397926\times10^3T_i- 22.55402644938806T_i^2+ 0.07675591177870559T_i^3-1.30465829788791\times 10^{-4}T_i^4+8.86065316687571\times10^{-8}T_F^5)-P_y,$$

wherein $P_y$ is a specified numerical value and takes a specific value of 0.5 MPa, 1 MPa, 2 MPa or 3 MPa, and it is guaranteed that $P_y<P_i$.

Simulated development is conducted on the hydrate systems with different buried depths by employing different pressures $P_{wi}$, and real-time variations of the gas production rate $V_g$ and the water production rate $M_w$ of each system in the development process is monitored and collected in real time.

When hydrate disturbance caused by human development under depressurization is simulated, the gas production rates $V_g$ and the water production rates $M_w$ of the hydrate systems in the experimental process can be increased gradually. The stability of the hydrate reservoirs with different buried depths is analyzed based on the gas production rates $V_g$ and the water production rates $M_w$ as follows:

if the gas production rates $V_g$ and the water production rates $M_w$ of the hydrate systems with different buried depths in the decomposition process are similar, it shows that the productivity advantages of the hydrate systems with different buried depths during decomposition under depressurization to the same degree are similar, and thus the effect of a depth or a temperature pressure of a reservoir on the productivity is limited;

if the gas production rate $V_g$ of the hydrate system with a certain buried depth is increased more quickly, it represents that the gas production potential of the hydrate system with the buried depth is relatively high correspondingly; if the gas production rate $V_g$ shows variations in different stages, it shows that the hydrate systems with different buried depths have the staged gas production ability in the process of depressurization to the same degree;

laws of water production of the hydrate systems with different buried depths are analyzed through $$R_{GNW} = \frac{V_g * M_{in}}{M_w},$$

wherein $M_{in}$ is the quantity of the deionized water injected when the hydrate systems with the corresponding buried depths are prepared, with the unit of mL; and the larger $R_{GNW}$ is, it shows that the better the relative economy of developing the hydrate systems with the corresponding buried depths is.

Embodiment 1

Figure 1:
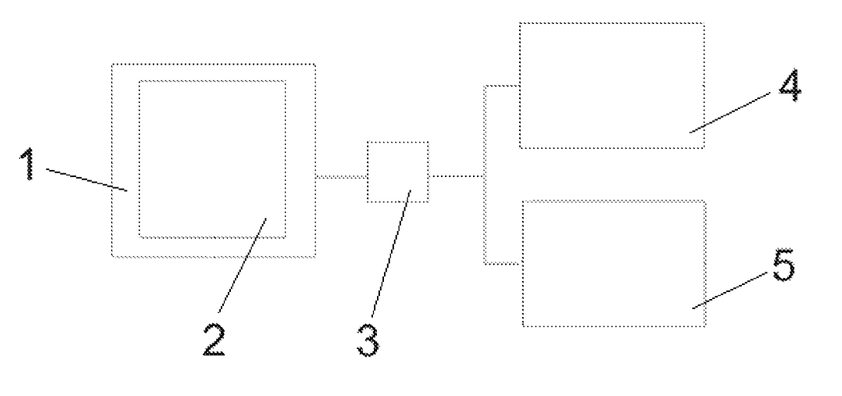
FIG. 1 is a structural schematic diagram of a device for implementing disturbance decomposition process of hydrates.

As shown in FIG. 1, a device for implementing the disturbance decomposition process of hydrates comprises a temperature control system 1, a hydrate preparation system 2, a depressurization control system 3, a gas production metering system 4 and a water production metering system 5. The hydrate preparation system 2 comprises a reaction kettle. In the reaction kettle, a temperature of the hydrate preparation system 2 is controlled with the temperature control system 1, so that the hydrates are synthesized from methane gas, deionized water and sediment. Meanwhile, with the temperature control system 1 and the depressurization control system 3, disturbance decomposition of the hydrates in the hydrate preparation system is achieved; the gas production rate $V_g$ in the disturbance decomposition process of the hydrates is metered with the gas production metering system 4; and the water production rate $M_w$ in the disturbance decomposition process of the hydrates is metered with the water production metering system 5.

In this embodiment, hydrate disturbance caused by tectonic movement, for example, strong tectonic uplift, fall of a sea level or other situations, in the natural environment is simulated with the device as shown in FIG. 1, and the hydrate systems are still under the phase equilibrium condition after disturbance. In this embodiment, the hydrate systems with three buried depths are employed, wherein A represents a shallow-buried hydrate system; B represents a medium-buried hydrate system; and C represents a deep-buried hydrate system.

In this embodiment, the disturbance and stability analysis method for hydrate reservoirs with the three buried depths comprises the following steps:

step 1, preparing a series of stable hydrate systems A, B and C parallel to the hydrate phase equilibrium condition in a vessel with a volume of $V_{hf}$, wherein the unit of $V_{hf}$ is L. Temperature values and pressure values of the prepared hydrate systems with the three buried depths are $(T_A, P_A)$, $(T_B, P_B)$ and $(T_C, P_C)$ respectively, wherein $T_A < T_B < T_C$; and the temperature values and pressure values of the hydrate systems with the three buried depths need to satisfy the following conditions:

$\ln(P_A) = -1.9413850446456 \times 10^5 + 3.31018213397926 \times 10^3 (T_A + T_t) - 22.5540264493806 (T_A + T_t)^2 + 0.0767559117787059 (T_A + T_t)^3 - 1.30465829788791 \times 10^{-4} (T_A + T_t)^4 + 8.86065316687571 \times 10^{-8} (T_A + T_t)^5;$ $\ln(P_B) = -1.9413850446456 \times 10^5 + 3.31018213397926 \times 10^3 (T_B + T_t) - 22.5540264493806 (T_B + T_t)^2 + 0.0767559117787059 (T_B + T_t)^3 - 1.30465829788791 \times 10^{-4} (T_B + T_t)^4 + 8.86065316687571 \times 10^{-8} (T_B + T_t)^5;$ $\ln(P_C) = -1.9413850446456 \times 10^5 + 3.31018213397926 \times 10^3 (T_C + T_t) - 22.5540264493806 (T_C + T_t)^2 + 0.0767559117787059 (T_C + T_t)^3 - 1.30465829788791 \times 10^{-4} (T_C + T_t)^4 + 8.86065316687571 \times 10^{-8} (T_C + T_t)^5.$ wherein $T_t$ is a specified numerical value with the unit of ° C.

The preparation process of the stable hydrate systems with the three buried depths comprises the following steps:

firstly, filling a cleaned and dried reaction kettle with a known volume $V_{hf}$ with sediment with a known density, compacting the sediment, and recording a weight M of the filled sediment, wherein the unit of $V_{hf}$ is mL, and the unit of M is g; covering the reaction kettle with a kettle cover; after purging with methane gas for several times, continuously injecting pure methane gas; controlling the content of the methane gas entering the reaction kettle with a gas flowmeter at $V_{CH4}$, and at this time, obtaining the molar mass of the methane gas injected into the system: $n_{CH4} = V_{CH4}/22.4$; closing an injection valve of the reaction kettle, setting a temperature of the system as a room temperature, and waiting for the system to be stabilized; and when preparing the hydrate systems with different buried depths, enabling the injection quantities M of the sediment and the injection quantities $n_{CH4}$ of the methane gas to be the same.

Then, opening the injection valve again, and injecting deionized water into the reaction kettle with the injection quantity of $V_{wi}$ (the injection quantities of the deionized water for the hydrate systems with different buried depths are different, and with increase in buried depth of the hydrate systems, the injection quantity of the deionized water is increased), wherein i=A, B, C; after closing the valve and waiting for the system to be stabilized, cooling the reaction kettle to 0.5° C.; and after hydrates are synthesized and the hydrate systems are finally stabilized, recording an average temperature $T_{hdi}$ and a pressure $P_{hdi}$ of each system at this time, wherein the unit $T_{hdi}$ of is ° C.; the unit $P_{hdi}$ of is MPa; and the unit $V_{wi}$ of is mL.

In the above steps, a measuring standard of the injection quantity $V_{wi}$ of the deionized water is $$\frac{V_{wi}}{18} \geq 6 n_{CH_4},$$

and the system pressure condition $P_{hdi} > P_{ei}$ is guaranteed with the injection quantity after the hydrates are synthesized, wherein $P_{ei}$ is a corresponding hydrate phase equilibrium pressure at the system average temperature $T_{hdi}$; and a calculating formula of $P_{ei}$ is as follows:

$$\ln(P_{ei}) = a_0 + a_1 T + a_2 T^2 + a_3 T^3 + a_4 T^4 + a_5 T^5, \quad (1)$$

wherein $T=T_{hdi}+273.15$ the unit of T is K; and $a_0$-$a_5$ take values under the following conditions:

$$\begin{cases} a_0 = -1.94138504464560 \times 10^5 \\ a_1 = 3.31018213397926 \times 10^3 \\ a_2 = -2.25540264493806 \times 10^1 \\ a_3 = 7.67559117787059 \times 10^{-2} \\ a_4 = -1.30465829788791 \times 10^{-4} \\ a_5 = 8.86065316687571 \times 10^{-8} \end{cases} 0° C. \leq T_{hdi} \leq 25° C.,$$

$$\begin{cases} a_0 = -4.38921173434628 \times 10^1 \\ a_1 = 7.76302133739303 \times 10^{-1} \\ a_2 = -7.27291427030502 \times 10^{-3} \\ a_3 = 3.85413985900724 \times 10^{-5} \\ a_4 = -1.03669656828834 \times 10^{-7} \\ a_5 = 1.09882180475307 \times 10^{-10} \end{cases} -25° C. \leq T_{hdi} \leq 0° C.$$

Finally, through the formula (1), reversely solving a corresponding equilibrium temperature $T_{ei}$ at a system stabilization pressure $P_{hdi}$, slowly raising the temperature of each system to ($T_{ei}-T_t$) at a rate of 1/4-2° C./h; wherein $T_t$ is a specific numerical value, and $T_t<T_{ei}$; and at this time, a final average temperature of the formed hydrate systems with different buried depths is $T_i=T_{endi}=T_{ei}-T_t$, and the pressure is $P_i=P_{hdi}$.

Step 2, disturbing the hydrate systems with the three buried depths A, B and C prepared in the step 1, and collecting the gas production rates $V_g$ and the water production rates $M_w$ of the systems under disturbance. In this embodiment, the hydrate systems are disturbed through two modes of heating disturbance and depressurization disturbance.

When heating disturbance is conducted on the hydrate systems, the temperatures of the hydrate systems with the three buried depths are sequentially raised to $T_i+1$, $T_i+2$ until to $T_i+T_t$ with the temperature control system 1 at a heating rate of 1° C./h; the temperature is kept for 12 h or above if the required consumed time is $T_t$; and at this time, the hydrate systems with different buried depths are still under the phase equilibrium condition. In the heating and temperature stabilization process, the variation situations of the gas production rates $V_g$ of the hydrate systems with different buried depths in the disturbance process are monitored and collected by using the gas production metering system 4, wherein the unit of the gas production rates $V_g$ is L; and the variation situations of the water production rates $M_w$ of the hydrate systems with different buried depths in the disturbance process are monitored and collected by using the water production metering system, wherein the unit of the gas production rates $M_w$ is g.

When depressurization disturbance is conducted on the hydrate systems, the hydrate systems with the three buried depths are subjected to depressurization disturbance by using the depressurization control system 3, and the pressure $P_{hdi}$ of each hydrate system is lowered to $P_{wi}$. In the depressurization disturbance process, different depressurization rates or staged depressurization may be employed, the disturbed hydrate systems are still under the phase equilibrium condition, and then $P_{wi}$ meets the following requirement:

$P_{wA}=\exp(-1.9413850446456\times10^5+$
$3.31018213397926\times10^3 T_A-$
$22.5540264493806 T_A^2+$
$0.0767559117787059 T_A^3-1.30465829788791\times$
$10^{-4} T_A^4+8.86065316687571\times10^{-8} T_A^5)$ $P_{wB}=\exp(-1.9413850446456\times10^5+$
$3.31018213397926\times10^3 T_B-$
$22.5540264493806 T_B^2+$
$0.0767559117787059 T_B^3-1.30465829788791\times$
$10^{-4} T_B^4+8.86065316687571\times10^{-8} T_B^5)$ $P_{wC}=\exp(-1.9413850446456\times10^5+$
$3.31018213397926\times10^3 T_C-$
$22.5540264493806 T_C^2+$
$0.0767559117787059 T_C^3-1.30465829788791\times$
$10^{-4} T_C^4+8.86065316687571\times10^{-8} T_C^5)$ When the hydrate systems with different buried depths are disturbed under different depressurization conditions, the gas production rates $V_g$ and the water production rates $M_w$ of the systems under disturbance are collected.

Step 3, analyzing the stability of the hydrate reservoirs with different buried depths based on real-time variable quantities of the gas production rates $V_g$ and the water production rates $M_w$.

if Vg and Mw are increased slowly, $$\Delta \frac{V_g}{V_{hf}} < 0.1 \text{ L/h},$$

$\Delta M_w \leq 1$ g/min, or Vg and Mw are invariable, it shows that the hydrates are stable when the hydrate systems with the corresponding buried depths are disturbed under the hydrate phase equilibrium condition; and If $V_g$ and $M_w$ are increased continuously, it shows that the system is unstable when the hydrate systems with the corresponding buried depths are disturbed under the hydrate phase equilibrium condition. Further, the larger the increasing rates of $V_g$ and $M_w$ are, the poorer the stability of the hydrate systems with the corresponding buried depths is. If $V_g$ and $M_w$ show variations in different stages, it shows there is a staged difference in stability of the hydrate system with the corresponding buried depth.

Comparing the hydrate systems with different buried depths, if Vg varies significantly, $$\Delta \frac{V_g}{V_{hf}} < 0.1 \text{ L/h},$$

Mw does not vary obviously, and $\Delta M_w \leq 1$ g/min, it shows that when the hydrate systems with the corresponding buried depths are still in the phase equilibrium condition under natural disturbance, decomposition can occur, and there is a risk of gas leakage; if Mw varies obviously, $\Delta M_w > 1$ g/min, Vg does not vary significantly, and $$\Delta \frac{V_g}{V_{hf}} < 0.1 \text{ L/h},$$

it shows that the hydrate systems with the corresponding buried depths are not decomposed when being still in the phase equilibrium condition under natural disturbance; but the salinity of seawater in a region can be changed due to production of water in a water saturation system, and the in-situ ecological environment is destroyed. Under the natural conditions, a coping strategy for destroying the undersea ecosphere by disturbance should be noted.

Embodiment 2

In this embodiment, disturbance due to human development with depressurization is simulated with the device as shown in FIG. 1, and disturbed hydrate systems are in an unstable state. In this embodiment, the hydrate systems with three buried depths are also employed, wherein D represents a shallow-buried hydrate system; E represents a medium-buried hydrate system; and F represents a deep-buried hydrate system.

In this embodiment, the disturbance and stability analysis method for hydrate reservoirs with the three different buried depths comprises the following steps:

step 1, according to the steps described in Embodiment 1, preparing the stable hydrate systems D, E, F with consistent system porosity and hydrate saturation under different buried depth conditions. Temperature values and pressure values of the prepared hydrate systems with the three buried depths are $(T_D, P_D)$, $(T_E, P_E)$ and $(T_F, P_F)$ respectively, wherein $T_D<T_E<T_F$. As the above three stable hydrate systems are parallel to the hydrate phase equilibrium condition, the corresponding temperature values and the corresponding pressure values of the prepared hydrate systems with different buried depths need to satisfy the following conditions:

$$\ln(P_D) = -1.9413850446456 \times 10^5 + 3.31018213397926 \times 10^3(T_D+T_y) - 22.5540264493806(T_D+T_y)^2 + 0.0767559117787059(T_D+T_y)^3 - 1.30465829788791 \times 10^{-4}(T_D+T_y)^4 + 8.86065316687571 \times 10^{-8}(T_D+T_y)^5;$$

$$\ln(P_E) = -1.9413850446456 \times 10^5 + 3.31018213397926 \times 10^3(T_E+T_y) - 22.5540264493806(T_E+T_y)^2 + 0.0767559117787059(T_E+T_y)^3 - 1.30465829788791 \times 10^{-4}(T_E+T_y)^4 + 8.86065316687571 \times 10^{-8}(T_E+T_y)^5;$$

$$\ln(P_F) = -1.9413850446456 \times 10^5 + 3.31018213397926 \times 10^3(T_F+T_y) - 22.5540264493806(T_F+T_y)^2 + 0.0767559117787059(T_F+T_y)^3 - 1.30465829788791 \times 10^{-4}(T_F+T_y)^4 + 8.86065316687571 \times 10^{-8}(T_F+T_y)^5;$$

Step 2, conducting depressurization disturbance on the hydrate systems D, E, F prepared in the step 1. In this embodiment, disturbance decomposition of the hydrate systems with different buried depths is achieved with depressurization disturbance.

Decompositions of the hydrate systems with different buried depths under depressurization to the same degree are simulated by using the depressurization control system 3; and decomposition pressures applied to the hydrate systems with different buried depths are $P_{wi}$ (i=D, E, F) and satisfy the following conditions:

$$P_{wD} = \exp(-1.9413850446456 \times 10^5 + 3.31018213397926 \times 10^3 T_D - 22.5540264493806 T_D^2 + 0.0767559117787059 T_D^3 - 1.30465829788791 \times 10^{-4} T_D^4 + 8.86065316687571 \times 10^{-8} T_D^5) - P_y;$$

$$P_{wE} = \exp(-1.9413850446456 \times 10^5 + 3.31018213397926 \times 10^3 T_E - 22.5540264493806 T_E^2 + 0.0767559117787059 T_E^3 - 1.30465829788791 \times 10^{-4} T_E^4 + 8.86065316687571 \times 10^{-8} T_E^5) - P_y;$$

$$P_{wF} = \exp(-1.9413850446456 \times 10^5 + 3.31018213397926 \times 10^3 T_F - 22.5540264493806 T_F^2 + 0.0767559117787059 T_F^3 - 1.30465829788791 \times 10^{-4} T_F^4 + 8.86065316687571 \times 10^{-8} T_F^5) - P_y;$$

In the formula, $P_y$ may take a specific value of 0.5 MPa, 1 MPa, 2 MPa or 3 MPa, and it is guaranteed that $P_y<P_i$.

Step 3, conducting simulated development on the hydrate systems with different buried depths by employing different pressures $P_{wi}$, and recording real-time variations of the gas production rate $V_g$ and the water production rate $M_w$ of each hydrate system in the simulated development process.

Different from Embodiment 1, in the simulated experimental process of the hydrate systems D, E, F with different buried depths, $V_g$ and $M_w$ can be increased gradually; and the stability of the hydrate systems with different buried depths are judged based on the increase situations.

If the gas production rates $V_g$ and the water production rates $M_w$ of the hydrate systems D, E, F with different buried depths in the decomposition process are similar, it shows that the productivity advantages of the hydrate systems with different buried depths during decomposition under depressurization to the same degree are similar, and thus the effect of a depth or a temperature pressure of a reservoir on the productivity is limited.

If the gas production rate $V_g$ of the hydrate system with a certain buried depth is increased more quickly, it represents that the gas production potential of the hydrate system with the buried depth is relatively high correspondingly; if the gas production rate $V_g$ shows variations in different stages, it shows that the hydrate systems with different buried depths have the staged gas production ability in the process of depressurization to the same degree.

When the water production laws of the hydrate systems D, E, F are analyzed, system standardized water production $$M_{NW} = \frac{M_w}{M_{in}}$$

is introduced, wherein $M_{in}$ is the quantity of deionized water injected when the hydrate systems with different buried depths are prepared.

By comprehensively comparing $$R_{GNW} = \frac{V_g}{M_{NW}} = \frac{V_g * M_{in}}{M_W},$$

the larger $R_{GNW}$ is, it shows that the better the relative economy of developing the hydrate systems with the corresponding buried depths is.

The others are the same as in Embodiment 1.

What is claimed is:

1. A disturbance and stability analysis method for hydrate reservoirs with different buried depths, comprising the following steps:
    S1: preparing a series of stable hydrate systems parallel to a hydrate phase equilibrium curve, wherein both of the porosities and the hydrate saturations of various hydrate systems are consistent, but the buried depths are different; a temperature value and a pressure value of each stable hydrate system are Ti and Pi respectively, wherein i represents each of stable hydrate systems i with different buried depths; and the corresponding temperature values and pressure values of the hydrate systems with different buried depths need to satisfy the following condition:

$$\ln(P_i) = -1.9413850446456 \times 10^5 + 3.31018213397926 \times 10^3(T_i+T_t) - 22.5540264493806(T_i+T_t)^2 + 0.0767559117787059(T_i+T_t)^3 - 1.30465829788791 \times 10^{-4}(T_i+T_t)^4 + 8.86065316687571 \times 10^{-8}(T_i+T_t)^5,$$

wherein $T_t$ is a specified numerical value with the unit of ° C.;

S2: disturbing the series of hydrate systems prepared in the first step, conducting disturbance under different conditions aiming to the hydrate systems with different buried depths, and monitoring and collecting the gas production rates Vg and the water production rates Mw of the systems under disturbance;

S3: analyzing the stability of the hydrate reservoirs with different buried depths based on real-time variable quantities of the gas production rates Vg and the water production rates Mw;

in the step S1, the preparation process of the stable hydrate systems comprises the following steps:

S1.1: filling a cleaned and dried reaction kettle with a known volume Vhf with sediment with a known density, compacting the sediment, recording a weight of the filled sediment, and covering the reaction kettle with a kettle cover; after purging with methane gas for several times, continuously injecting pure methane gas; controlling the content of the methane gas entering the reaction kettle with a gas flowmeter at VCH4, and at this time, obtaining the quantity of the methane gas substance injected into the system: nCH4=VCH4/22.4; closing an injection valve of the reaction kettle, setting a temperature of a system as the room temperature, and waiting for the system to be stabilized; and when preparing the hydrate systems with different buried depths, enabling the injection quantities of the sediment and the injection quantities of the methane gas to be the same, wherein the unit of VCH4 is mL, and the unit of nCH4 is mol;

S1.2: opening the injection valve again, and injecting deionized water into the reaction kettle with the injection quantity of $V_{wi}$, the injection quantities of the deionized water for the hydrate systems with different buried depths are different, and with increase in buried depth of the hydrate systems, the injection quantity of the deionized water is increased; after closing the valve and waiting for the system to be stabilized, cooling the reaction kettle to 0.5° C.; and after hydrates are synthesized and the hydrate systems are finally stabilized, recording an average temperature Thdi and a pressure Phdi of each system at this time, wherein the unit of Thdi is ° C., the unit of Phdi is MPa and the unit of Vwi is mL;

wherein a measuring standard of the injection quantity Vwi of the deionized water is $$\frac{V_{wi}}{18} \geq 6n_{CH_4},$$

and the system pressure condition Phdi>Pei is guaranteed with the injection quantity after the hydrates are synthesized, wherein Pei is a corresponding hydrate phase equilibrium pressure at the system average temperature Thdi, and a calculating formula of Pei is as follows:

$$\ln(P_{ei}) = a_0 + a_2 T^2 + a_3 T^3 + a_4 T^4 + a_5 T^5, \quad (1)$$

wherein $T = T_{hdi} + 273.15$, the unit of T is K; and a0-a5 take values under the following conditions:

$$\begin{cases} a_0 = -1.94138504464560 \times 10^5 \\ a_1 = 3.31018213397926 \times 10^3 \\ a_2 = -2.25540264493806 \times 10^1 \\ a_3 = 7.67559117787059 \times 10^{-2} \\ a_4 = -1.30465829788791 \times 10^{-4} \\ a_5 = 8.86065316687571 \times 10^{-8} \end{cases} \quad 0° C. \leq T_{hdi} \leq 25° C.,$$

-continued $$\begin{cases} a_0 = -4.38921173434628 \times 10^1 \\ a_1 = 7.76302133739303 \times 10^{-1} \\ a_2 = -7.27291427030502 \times 10^{-3} \\ a_3 = 3.85413985900724 \times 10^{-5} \\ a_4 = -1.03669656828834 \times 10^{-7} \\ a_5 = 1.09882180475307 \times 10^{-10} \end{cases} \quad -25° C. \leq T_{hdi} \leq 0° C.$$

S1.3: through the formula (1), reversely solving a corresponding equilibrium temperature Tei at a system stabilization pressure Phdi, slowly raising the temperature of each system to (Tei−Tt) at a rate of 1/4-2° C./h; wherein Tt is a specific numerical value, and Tt<Tei; and at this time, a final average temperature of the hydrate systems with different buried depths is Ti=Tendi=Tei−Tt, and the pressure is Pi=Phdi.

2. The disturbance and stability analysis method for the hydrate reservoirs with different buried depths according to claim 1, wherein when heating disturbance is conducted on the stable hydrate systems with different buried depths by simulating hydrate disturbance caused by tectonic movement in the natural environment, the temperatures of the series of stable hydrate systems prepared in the step S1 are slowly raised to (Ti+Tt) at a rate of 1/2-1° C./h, and the temperature is kept for 12 h or above, wherein Tt is the specified numerical value; at this time, the hydrate systems are still under the phase equilibrium condition; and in the whole heating and temperature stabilizing process, the gas production rate Vg and the water production rate Mw of each system under disturbance are monitored and collected in real time.

3. The disturbance and stability analysis method for the hydrate reservoirs with different buried depths according to claim 1, wherein in the step S2, when depressurization disturbance is conducted on the stable hydrate systems with different buried depths by simulating hydrate disturbance caused by tectonic movement in the natural environment, a system pressure value Pi of each hydrate system is lowered to Pwi; and if hydrates after being disturbed are under the phase equilibrium condition, Pwi satisfies the following condition:

$$P_{wi} = \exp(-1.9413850446456 \times 10^5 + 3.31018213397926 \times 10^3 T_i - 22.5540264493806 T_i^2 + 0.0767559117787059 T_i^3 - 1.30465829788791 \times 10^{-4} T_i^4 + 8.86065316687571 \times 10^{-8} T_i^5);$$

in the depressurization disturbance process, the gas production rate Vg and the water production rate Mw of each system under disturbance are monitored and collected in real time.

4. The disturbance and stability analysis method for the hydrate reservoirs with different buried depths according to claim 1, wherein in the step S2, when hydrate disturbance caused by human development under depressurization is simulated, decompositions of the hydrate systems with different buried depths under depressurization to the same degree are simulated; and decomposition pressures applied to the hydrate systems with different buried depths are Pwi, and Pwi satisfies the following condition:

$$P_{wi} = \exp(-1.9413850446456 \times 10^5 + 3.31018213397926 \times 10^3 T_i - 22.5540264493806 T_i^2 + 0.0767559117787059 T_i^3 - 1.30465829788791 \times 10^{-4} T_i^4 + 8.86065316687571 \times 10^{-8} T_F^5) - P_y,$$

wherein Py is a specified numerical value and takes a value of 0.5 MPa, 1 MPa, 2 MPa or 3 MPa, and Py<Pi;

simulated development is conducted on the hydrate systems with different buried depths by employing different pressures Pwi, and real-time variations of the gas production rate Vg and the water production rate Mw of each system in the development process is monitored and collected in real time, wherein the unit of the gas production rate Vg is L; and the unit of the water production rate Mw is g.

5. The disturbance and stability analysis method for the hydrate reservoirs with different buried depths according to claim 1, wherein in the step S3, when hydrate disturbance caused by tectonic movement in the natural environment is simulated, the stability of the hydrate reservoirs with different buried depths is analyzed based on the gas production rates Vg and the water production rates Mw as follows:

if Vg and Mw are increased slowly, $$\Delta \frac{V_g}{V_{hf}} < 0.1 \text{ L/h},$$

$\Delta M_w \leq 1$ g/min, or Vg and Mw are invariable, it shows that the hydrates are stable when the hydrate systems with the corresponding buried depths are disturbed under the hydrate phase equilibrium condition; and if Vg and Mw are increased continuously, it shows that the hydrates are unstable when the hydrate systems with the corresponding buried depths is disturbed under the hydrate phase equilibrium condition;

comparing the hydrate systems with different buried depths, if Vg varies significantly, $$\Delta \frac{V_g}{V_{hf}} < 0.1 \text{ L/h},$$

Mw does not vary obviously, and $\Delta Mw \leq 1$ g/min, it shows that when the hydrate systems with the corresponding buried depths are still in the phase equilibrium condition under natural disturbance, decomposition can occur, and there is a risk of gas leakage; if Mw varies obviously, $\Delta M_w > 1$ g/min, Vg does not vary significantly, and $$\Delta \frac{V_g}{V_{hf}} < 0.1 \text{ L/h},$$

it shows that the hydrate systems with the corresponding buried depths are not decomposed when being still in the phase equilibrium condition under natural disturbance; but the salinity of seawater in a region can be changed due to production of water in a water saturation system, and the in-situ ecological environment is destroyed.

6. The disturbance and stability analysis method for the hydrate reservoirs with different buried depths according to claim 1, wherein in the step S3, when the hydrates are disturbed by simulating human development under depressurization, the stability of the hydrate reservoirs with different buried depths is analyzed based on the gas production rates Vg and the water production rates Mw as follows:

if the gas production rates Vg and the water production rates Mw of the hydrate systems with different buried depths in the decomposition process are similar, it shows that the productivity advantages of the hydrate systems with different buried depths during decomposition under depressurization to the same degree are similar, and thus the effect of a depth or a temperature pressure of a reservoir on the productivity is limited;

if the gas production rate Vg of the hydrate system with a certain buried depth is increased more quickly, it represents that the gas production potential of the hydrate system with the buried depth is relatively high correspondingly; if the gas production rate Vg shows variations in different stages, it shows that the hydrate systems with different buried depths have the staged gas production ability in the process of depressurization to the same degree;

laws of water production of the hydrate systems with different buried depths are analyzed through $$R_{GNW} = \frac{V_g * M_{in}}{M_w},$$

wherein $M_{in}$ is the quantity of the deionized water injected when the hydrate systems with the corresponding buried depths are prepared, with the unit of mL; and the larger $R_{GNW}$ is, it shows that the better the relative economy of developing the hydrate systems with the corresponding buried depths is.

* * * * *